US010596280B1

(12) United States Patent
Henderson et al.

(10) Patent No.: US 10,596,280 B1
(45) Date of Patent: Mar. 24, 2020

(54) UV LED DISINFECTING FLOOR MAT

(71) Applicant: THE PATENT WELL LLC, Fort Worth, TX (US)

(72) Inventors: Jeb Henderson, Fort Worth, TX (US); Mike Dry, Fort Worth, TX (US); Kelly Templin, Granbury, TX (US); Jeff Busby, Millsap, TX (US)

(73) Assignee: The Patent Well LLC, Fort Worth, TX (US)

( * ) Notice: Subject to any disclaimer, the term of this patent is extended or adjusted under 35 U.S.C. 154(b) by 0 days.

(21) Appl. No.: 15/993,238

(22) Filed: May 30, 2018

Related U.S. Application Data

(60) Provisional application No. 62/512,471, filed on May 30, 2017.

(51) Int. Cl.
*A61L 2/10* (2006.01)
*A47L 23/26* (2006.01)

(52) U.S. Cl.
CPC .............. *A61L 2/10* (2013.01); *A47L 23/266* (2013.01); *A47L 2601/10* (2013.01)

(58) Field of Classification Search
CPC ....... A61L 2/10; A47L 23/266; A47L 2601/10
USPC ... 250/453.11, 454.11, 455.11, 493.1, 494.1, 250/504 R
See application file for complete search history.

(56) References Cited

U.S. PATENT DOCUMENTS 6,828,576 B2 12/2004 Spivak
8,662,705 B2 3/2014 Roberts
9,144,617 B2 9/2015 Deng
9,579,410 B2 2/2017 Simmons et al.
2012/0167325 A1 7/2012 Omidi
2014/0239710 A1 8/2014 Salter et al.
2014/0288351 A1* 9/2014 Jones ................. A61N 5/06
  600/9
2015/0096597 A1* 4/2015 Patel ................. A47L 23/266
  134/18

FOREIGN PATENT DOCUMENTS

WO  20150157499  10/2015

OTHER PUBLICATIONS

FDC1004. Basics of Capacitive Sensing and Applications, Application Report SN)A927—Dec. 2014, Texas Instruments, 12 pages Dec. 31, 2014.
www.aliexpress.com, 16×16 RGB flexible LED matrix light, rgb led panel light, led display screen, AliExpress, 10 pages Dec. 31, 2016.

* cited by examiner

*Primary Examiner* — Nicole M Ippolito
(74) *Attorney, Agent, or Firm* — Jackson Walker, LLP

(57) ABSTRACT

Disinfecting floor mats may be achieved by a variety of systems, processes, and techniques. In one general implementation, a disinfecting floor mat may include a UV LED array, a base, and a transparent cover. The UV LED array may have a top surface, a bottom surface, a perimeter and include multiple UV-emitting LEDs. The base may be configured to receive the UV LED array. The transparent protective cover may include a top surface of an encapsulating sheet for encapsulating the array or a top surface of a non-encapsulated protective sheet, the cover comprised of polyurethane and having substantial strength to withstand a person standing directly thereon with shoes on. The LED array is adapted to irradiate at least a portion of a bottom surface of a shoe positioned on the protective cover.

13 Claims, 4 Drawing Sheets

UV LED DISINFECTING FLOOR MAT

RELATED APPLICATIONS

This is a utility application, which claims the benefit of U.S. Provisional Patent Application No. 62/512,471, filed May 30, 2017. This prior application is herein incorporated by reference in its entirety.

This utility application also incorporates by reference U.S. Pat. No. 8,662,705, issued Mar. 5, 2014; U.S. Pat. No. 9,144,617, issued Sep. 29, 2015; U.S. Pat. No. 6,828,576, issued Dec. 7, 2004; U.S. Pat. No. 7,229,516, issued Jun. 12, 2007; and U.S. Patent Pub. No. 2014/0239710, published Aug. 28, 2014.

FIELD OF THE INVENTION

Floor mats, namely, floor mats for disinfecting shoes.

BACKGROUND OF THE INVENTION

Floors, ground, or other support surfaces that are intended to be walked upon or stood on typically are covered with germs and other pathogens. One of the most common places superbugs, such as MRSA, can attach themselves to us and enter our bodies is through being picked up on our feet. A simple, easy method of disinfecting the shoes of the wearer would help reduce the pathogens carried on the shoes, especially if a floor mat capable of performing that function was provided outside a clean area. With a floor mat upon which one is standing, a shoe-wearing person could achieve disinfection or reduction of pathogens on the surface of the shoe sole before they entered a clean area.

SUMMARY OF THE INVENTION

A floor mat for disinfecting a shoe bottom including, in some embodiments, a rigid or flexible UV LED array having a top surface, a bottom surface, a perimeter and further including multiple UV emitting LED bulbs; a base for receiving the UV LED array, in some embodiments; a transparent protective cover including a top surface of an encapsulating sheet for encapsulating the array or a top surface of a non-encapsulated protective sheet; and a power source engaging the UV LED array. In certain embodiments, the encapsulating sheet of the protective cover is an elastomer (e.g., a cured, two-part polyurethane or an equivalent).

The floor mat may further include a pressure switch for activating the UV LED array, the pressure switch responsive to a weight on the protective cover.

DETAILED DESCRIPTION

Figure 1:
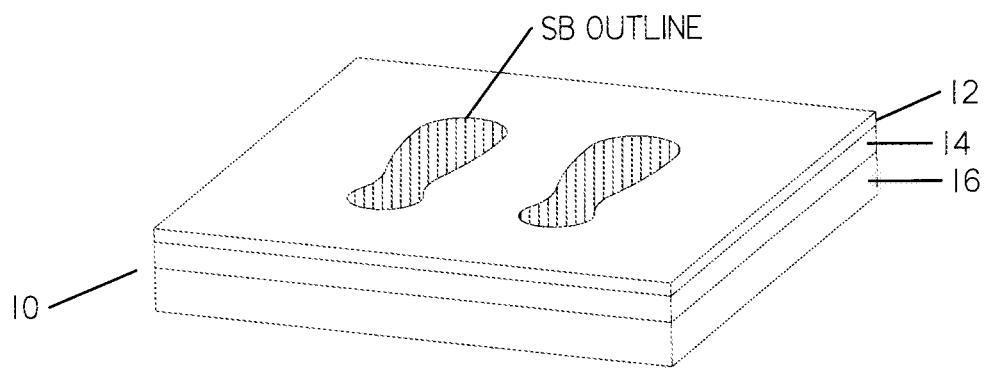
FIG. 1 is a perspective view of an example disinfecting floor mat.
Figure 2A:
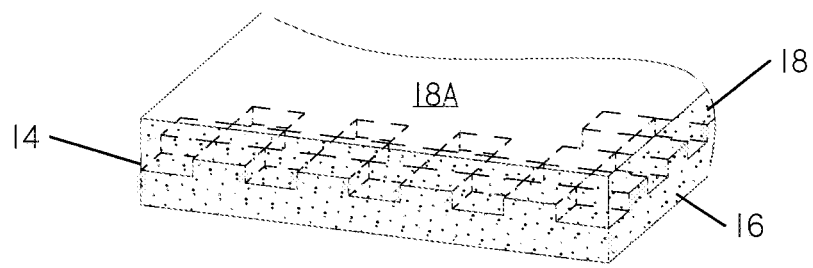
FIG. 2A is a detailed view of an LED array encapsulated for use with the floor mat.
Figure 2B:
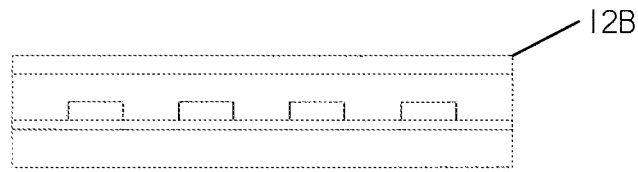
FIG. 2B is a cross-section of the UV LED array with a protective sheet thereon.

FIGS. 1, 2A, 2B, 2C, and 3 illustrate an example UV disinfecting floor mat 10 ("floor mat"). Floor mat 10 may include an LED array 14, which may be flexible or rigid and may have a top surface 14a, multiple UV emitting LEDs 14b, and multiple leads 14c extending therefrom, the leads intended to engage a power source, and, optimally, a controller (e.g., a microcontroller or a microprocessor) as set forth herein below.

Floor mat 10 may also include a base 16, which may be made from durable, rigid plastic or other suitable material or a semi-flexible material. In particular implementations, base 16 may be rolled into a cylinder shape. Base 16 includes a cutout 16a dimensioned to receive UV LED array 14, which may, as shown, be rectangular or any other appropriate configuration.

UV LED array 14 may be bare (non-encapsulated) and have a protective sheet 12 typically on or above top surface 14a of the bare UV LED array. Protective sheet 12 may be a separate sheet such as a durable, transparent, scuff-proof plastic, or protective sheet 12 may include the top surface 18a of an encapsulating body 18b of an encapsulating sheet 18. That is to say, bare UV LED array 14 may further comprise a transparent encapsulating sheet 18 with a protective top surface 18a that may simply be the top surface of encapsulating body 18b, body 18b encapsulating the multiple bulbs 14b of the LED array. Thus, LED array 14 may be a bare LED array with a protective sheet or one with a transparent encapsulating sheet 18. Moreover, a separate protective sheet 12 may be laid atop LED array, with or without the encapsulation sheet 18. While top surface 18a may include protective sheet 12, a separate protective sheet 12 is typically provided that is a scuff-proof, transparent—like body 12b of the encapsulating sheet is transparent—protective sheet 12 (or top surface 18a), being intended to receive the shoes thereon.

To be transparent, protective sheet 12 may be totally or partially clear with respect to visible light. Additionally, although it may block certain wavelengths of light, sheet 12 should allow at least certain UV light (e.g., UVC) to pass without significant degradation (e.g., greater than 90% transmission).

In some embodiments, protective sheet 12 may be tacky. Tack is a property whereby light contact with the surface of another body brings about a condition requiring force to restore the original separated state. It is a property that will inhibit but not wholly prevent the removal of a contacting surface or surfaces, such as opposing surfaces contacting each other under compression. Inherent tack means the surface possesses this property (tack) without requiring the addition of any further adhesion promoting component, or a tackifier. By being tacky, protective sheet 12 may trap dirt and contaminants, which may help to clean shoes better.

Because a tacky surface is likely to become dirty fairly quickly, which would likely inhibit the penetration of UV light therethrough, protective sheet 12 may be replaceable (e.g., on a weekly or as needed basis). Due to the inherent tackiness of the sheet, the sheet may be readily removed from and applied to body 18b.

Figure 3:
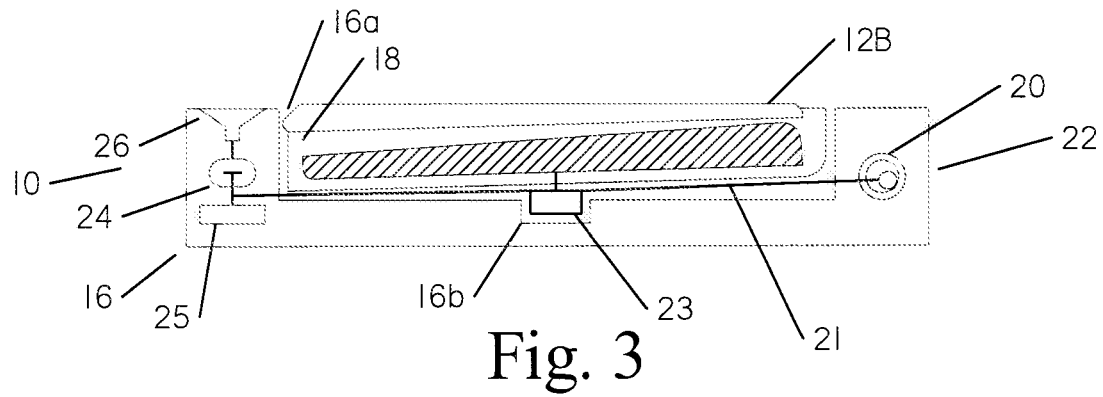
FIG. 3 is a cross-section of another example disinfecting floor mat showing details, including details of an electronic circuit and cover.
Figure 2C:
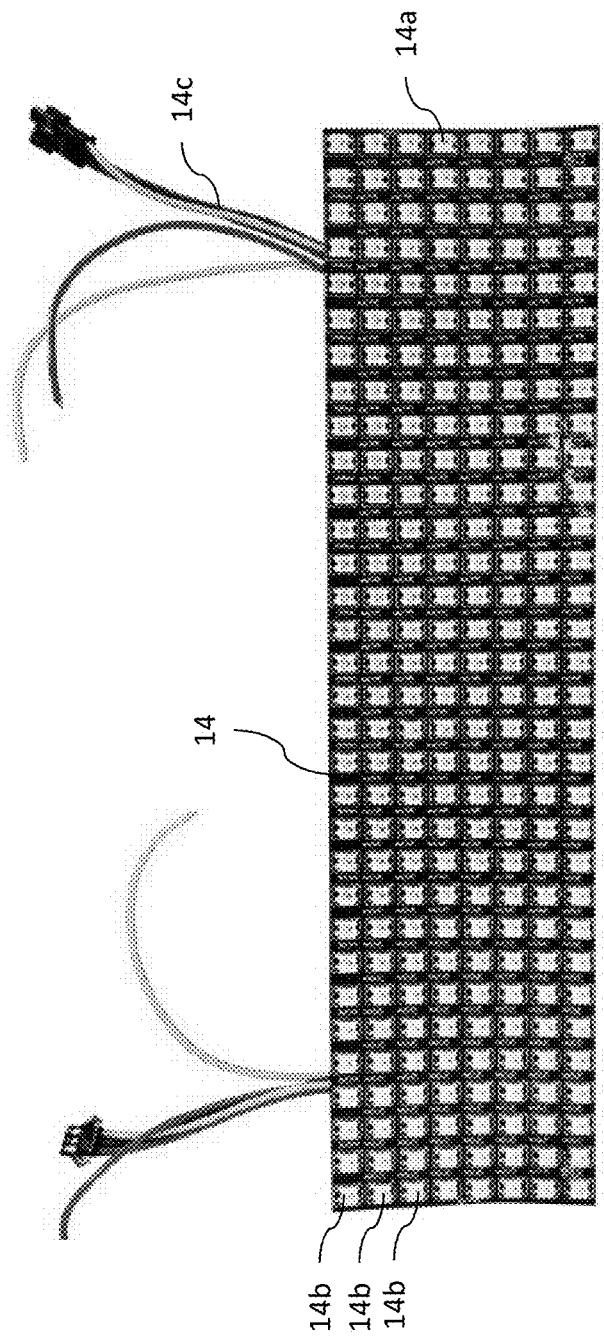
FIG. 2C is line drawing of an example UV LED array.

Base 16 is configured to receive in recess 16a the encapsulated or unencapsulated (with protective sheet) UV LED array 14 as seen in FIG. 3. It is further seen in FIG. 3 that base 16, in one embodiment, may have a cutout to contain batteries 20, and also may include an electrical circuit 21, a controller 25, a door 22 for accessing batteries, a switch 23, optionally, a timer 24 with a timer circuit, and a speaker 26.

Batteries 20 are intended to engage leads 14c through use of electrical circuit 21. Switch 23, which may, for example, be a pressure sensitive switch, may be placed in a cutout 16b in base 16 so as to extend partly thereabove. Switch 23 is typically placed below an outline of the shoe bottoms ("SB"), see FIG. 1, and may be set to a minimum close pressure, so that placement of a hand on the mat will not close it. Thus, a user may be around, over, or partially on the mat without it activating.

SB outline in FIG. 1 may simply be an indicia forming a first line in the shape of one foot and an indicia forming a second line in the shape of a second foot, the lines embossed or otherwise applied to transparent sheet 12 or top surface 18a. SB outline allows a user to stand in the designated spot, and with switch 23 located under one of the two feet (or both), circuit 21 may be energized with batteries 20 for energizing bulbs providing UV light (and, optionally, some visible light). The protective cover should be at least partially transparent. In a preferred embodiment, only the shoe outlined portion is transparent, the rest is opaque. The bulbs of the LEDs are at least under the shoe outline portion of the protective cover.

Optionally, electrical circuit 21 may include timer 24 or timer and a speaker 26. Timer 24 may initiate a timed circuit to maintain the closed circuit condition providing illumination to the UV LED bulbs 14b, such as for a period of 10 to 300 seconds. Timer 24 may include speaker 26 that emits an audible signal when the time circuit is completed and the LED lights are de-energized (open circuit condition) even if the user is still on mat 10, or even if the user has left mat 10, time circuit 24 allows the energized period to be responsive to an initial closed circuit condition initiated by pressure on pressure switch 23. Controller 25 can check switch condition for pressure or for timer complete and either timer complete or no pressure will dictate an open circuit. In some implementations, two pressure switches, one underneath each shoe outline, may be used, insuring a closed circuit when both feet are on the protective cover.

LED array 14 may be flexible or rigid. As shown, LED array is an 8×32 LED panel. Other sizes may be used in other implementations. In certain implementations, for example, LED array 14 is a flexible LED array and, in some embodiments, is a 16×16 RGB panel requiring low voltage DC, with, however, light emitting in the UV spectrum or at least partially in the UV spectrum. Controller 25 and electrical circuit 21 may selectively power individual bulbs as set forth in more detail below.

Body 18 (or protective sheet 12) may made of flexible material. For example, body 18 may be a cured polyurethane, which is commonly made by mixing a polyol with an isocyanate. Even in its general form, polyurethane typically allows some transmission of UV light. One composition that may be used is the two-part polyurethane found in U.S. Pat. No. 7,229,516 (Busby et al. Dec. 25, 2003), which is herein incorporated by reference.

In certain implementations, compositions may be added to the mixture to improve the transmission of UV light through the polyurethane. For example, an acrylic polyurethane blend could be used. The acrylic could, for instance, be blended with the polyol before it is combined with the isocyanate.

Body 18 (or protective sheet 12) may be relatively soft yet tough enough to withstand being walked on by humans wearing shoes. In certain implementations, body 18 may have a hardness between about 20-80 on the Shore OO scale.

A method of making the encapsulated body for the light emitting array may be found in the '516 patent, namely, FIGS. 8-13, wherein the "skeleton" of the gasket illustrated in the patent is the bare UV LED array 14 of this disclosure. Additionally, particular implementations may not use heat.

The following teachings related to UV LED lights and arrays are incorporated herein by reference: U.S. Pat. No. 9,144,617, issued Sep. 29, 2015; U.S. Pat. No. 8,662,705, issued Mar. 5, 2014; U.S. Pat. No. 6,828,576, issued Dec. 7, 2004; and U.S. Publication Number No. 2014/0239710 published Aug. 28, 2014.

This '617 patent discloses a method of disinfecting and lighting by using LEDs, using both lighting visible light LEDs and UV LEDs on a circuit board that mixes the two. The disinfecting properties of UV LED lights may be appreciated with respect to this reference.

The '705 patent discloses a flexible ultraviolet LED sanitizing apparatus that may be folded or rolled for storage and transport, and may be used as a sanitizing apparatus to sanitize a variety of objects beneath enclosure panels. This reference discloses the use of UVC light, which is ultraviolet electromagnetic radiation having a wavelength of about 100 nm to about 300 nm, and can provide 99.9% destruction of various organisms, including bacteria and influenza virus, in 60 seconds or less. In one embodiment, the UV LEDs emit at least some radiation in this range and some in the visible light range.

Similarly, the '576 patent discloses a UV LED light projection method and apparatus including UVC light band "germicidal UV". The '710 publication shows an illuminable auto floor mat that includes a visible light source that illuminates in the illuminable region, the visible light source being powered by a receiver that is wirelessly supplied by a transmitter.

Capacitive sensing technology exists for sensing human interface applications when a person initiates contact with the sensor electrodes—for example by finger touch. High performance contact sensing applications exist which may measure sensor contact against a baseline reference level of environmental conditions. Capacitive sensing has advantages over other detection approaches, such as optical detection methods, in its ability to sense different kind of materials (e.g., skin, plastic, leather, rubber, metal, liquid) and it may be contactless and wear free. See Texas Instruments application report SN0A927—December 2014 incorporated herein by reference. Thus, controller 25 may receive input from a membrane including such technology to sense a skin/no-skin condition. This will avoid UV illumination when skin is sensed (see FIG. 5).

Touch screen technology, such as capacitive or resistive touchscreen technology, can be used in conjunction with controller 25 to locate points of contact with the footwear (e.g., shoe). The controller then can selectively illuminate the UV LED lights at the same grid location that matches the pressure area. This will help minimize UV light leakage around areas outside the footwear.

Figure 4:
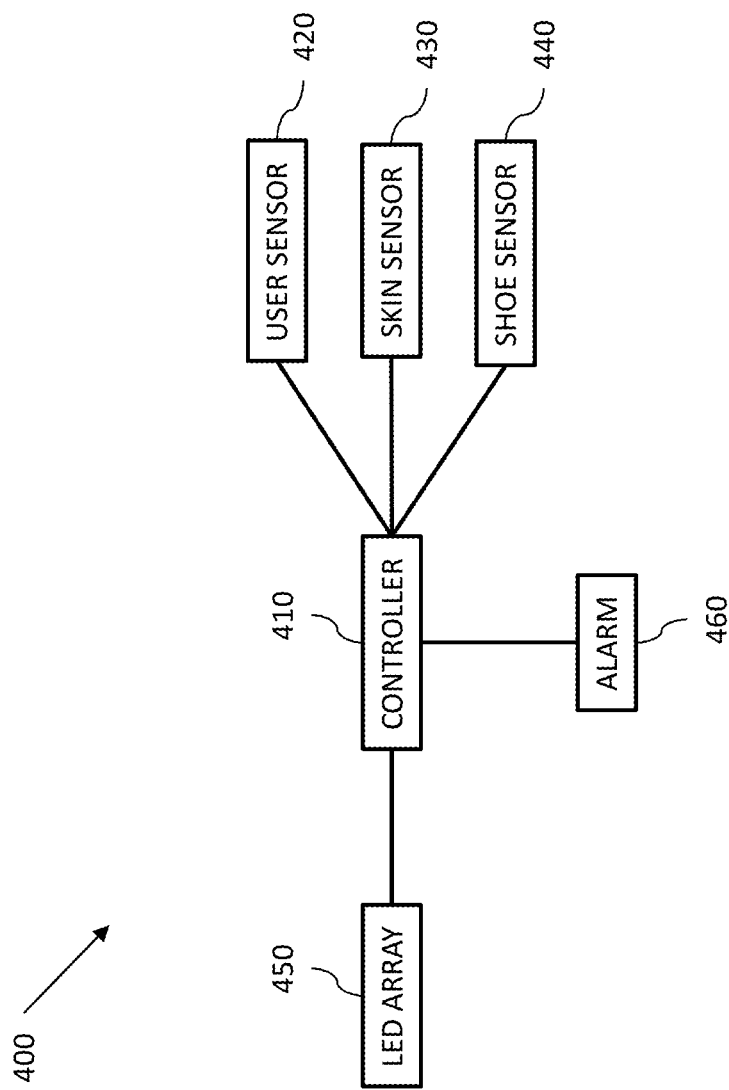
FIG. 4 is a block diagram illustrating selected components of an example control system for a disinfecting floor mat.

FIG. 4 illustrates selected components of an example control system 400 for a disinfecting floor mat. System 400 may, for example, be used for floor mat 10. Among other things, system 400 includes a controller 410, a user sensor 420, a skin sensor 430, a shoe sensor, and an LED array 450.

Controller 410 is responsible for the logical operation of system 400. Controller 410 may, for example, include a microprocessor, a microcontroller, a field-programmable gate array, or any other device for manipulating data in a logical manner. Controller 400 may also include instructions, whether in RAM, ROM, or otherwise, that dictate the logical operations.

Coupled to controller 410 is user sensor 420. User sensor 420 is adapted to sense when someone is present on the disinfecting floor mat. User sensor 420 may, for example, be a load cell or a pressure switch. In some implementations, user sensor 420 may be set so that it does not report to controller 410 unless the weight is above a certain level (e.g., 80 pounds). In other implementations, user sensor 420 may report the sensed weight to controller 410, and controller 410 may determine what operations to take based on the weight (e.g., to activate LED array 450 or not).

Also coupled to controller 410 is skin sensor 430. Skin sensor 430 is adapted to sense when someone's skin (e.g., foot or hand) is contacting the disinfecting floor mat. Skin sensor 430 may, for example, be a capacitive sensor. Using this information, controller 410 may determine whether to illuminate LEDs in LED array 450.

Also coupled to controller 410 is shoe sensor 440. Shoe sensor 440 is adapted to sense where someone's shoe is contacting the disinfecting floor mat. Shoe sensor 440 may, for example, be a number of pressure sensors (e.g., one associated with each LED). Using this information, controller 410 may determine which of LEDs in LED array 450 to illuminate.

Control system 400 also includes an alarm 460, which is coupled to controller 410. Controller 410 may activate alarm 460 for any of a variety of reasons (e.g., user is not wearing shoes). Alarm 460 may generate a visual and/or audible notification.

Other implementations may include fewer, greater, and/or a different arrangement of components. For example, a control system may not include a shoe sensor. For instance, if light is only allowed to pass through an outline of shoes on the protective cover, detecting the shoe bottoms may not be necessary, especially since UVC rays do not travel well in air. Similarly, some implementations may not include the skin sensor. In certain implementations, the floor mat may be powered by batteries or power from an electric grid. Particular implementations, may include a display (e.g., an LCD or LED screen) for communication information to a user or a user interface (e.g., touchscreen or a screen and a touchpad) for communicating information to and receiving information from a user.

Figure 5:
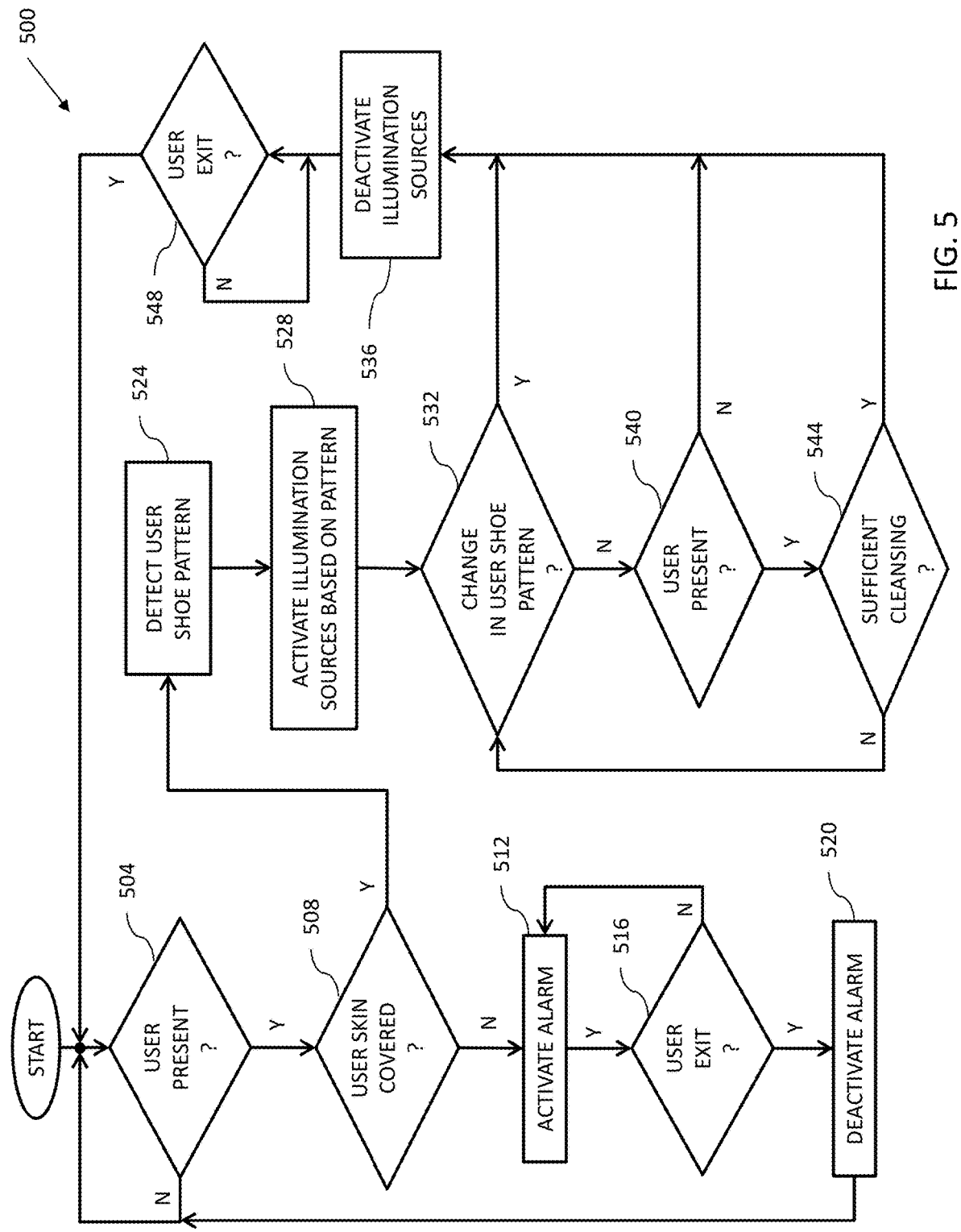
FIG. 5 is a flow diagram illustrating an example operational process for a disinfecting floor mat.

FIG. 5 illustrates example operations of a process 500 for operating a disinfecting floor mat. The operations may, for example, be controlled by controller 25 and include no skin condition and user presence detections (e.g., pressure above a preset 50# minimum), so casual contact with (e.g., with a bare hand) will not set off UV source, to create an "on" condition for the UV source (e.g., LED array). The "on" condition may be timed, for example, every 0.250 sec, for a pressure switch open condition or time out (about 30 sec-300 sec UV exposure). The pressure switch open condition on UV source cycle is provided so if a person steps off early, before time out, UV light shuts off.

Process 500 calls for determining whether a user is present (operation 504). Determining whether a user is present may, for example, be accomplished with a pressure-activated sensor. The pressure-activated sensor may be set to a minimum level (e.g., 50 pounds), which may help to ensure that the system does not active for accidental touches. Thus, a user may actually be on, around, or over the floor mat without being considered present by operation 504. If a user is not present, process 500 calls for continuing to wait for a user to be present.

Once a user is present, process 500 calls for determining whether the user's skin is covered (operation 508). Determining whether a user's skin is protected may, for example, be accomplished by capacitive-touch sensors, which may sense to bottom of the foot. If a user's skin is not protected, process 500 calls for activating an alarm (operation 512) and determining whether the user has exited (operation 516). The alarm may be a visual indicator (e.g., a warning light or a warning message) and/or an audible indicator (e.g., a bell, buzzer, siren, etc.). Determining whether the user has exited may be accomplished be sensing deactivation of a pressure switch. Once the user has exited, process 500 calls for deactivating the alarm (operation 520) and again detecting whether a user is present.

If the user's skin is protected, process 500 calls for detecting the user's shoe pattern (operation 524). Detecting a user's shoe pattern may, for example, be accomplished by using pressure activated sensors in the mat or capacitive sensing. Process 500 also calls for activating the illumination source based on the shoe pattern (operation 528). For example, only LEDs underneath the positions of the shoe pattern could be activated. For some shoes, the entire sole does not touch the ground (e.g., for heeled shoes). However, the UV light associated with the portions that do touch the ground may bleed over to these portions too, providing some disinfecting.

Process 500 calls for determining whether there is a change in shoe pattern (operation 532). This could, for example, occur by a user lifting their feet or rocking back and forth. If there is a change in shoe pattern, process 500 calls for deactivating the illumination sources (operation 536). As UV light is potentially harmful to humans, the system is designed to try to contain the light to the bottoms of the shoes as much as possible.

If there is no change in shoe pattern, process 500 calls for determining whether the user is present (operation 540). Again, as UV light is potentially harmful to humans, the system is designed to try to contain the light to the soles of the shoes as much as possible. Thus, if no user is present, the illumination sources are deactivated (operation 536).

If the user is present, process 500 calls for determining whether sufficient cleansing has occurred (operation 544). This may, for example, be accomplished based on time (e.g., 30 seconds). If sufficient cleansing has not occurred, process 500 calls for continuing to make sure that the user shoe pattern is remaining constant and that the user is present.

Once sufficient cleansing has occurred, process 500 calls for deactivating the illumination sources (operation 536). Process 500 also calls for waiting for the user to exit (operation 548). Process 500 then returns to determining whether a user is present (operation 504).

Although FIG. 5 illustrates one implementation of a process for operating a UV cleansing mat, other processes may include fewer, additional, and/or a different arrangement of operations. For example, a process may not call for detecting a user's shoe pattern. UVC light is known to degrade quickly in air. Thus, illuminating the entire mat may be possible. Additionally, if a change in user shoe pattern is detected, the illumination sources could be adjusted rather than deactivating all the illumination sources and requiring the user to reenter.

The floor mat may be used in locker rooms, surgery centers, medical supplies/equipment or food preparation or processing areas, nursing homes or anywhere where a clean room is required.

Although the invention has been described with reference to specific embodiments, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. A floor mat for disinfecting a shoe bottom, the floor mat comprising:
    a UV LED array having a top surface, a bottom surface, a perimeter and further comprising multiple UV emitting LEDs;
    a base for receiving the UV LED array;
    a transparent protective cover comprising a top surface of an encapsulating sheet for encapsulating the array or a top surface of a non-encapsulated protective sheet, the cover comprised of polyurethane and having substantial strength to withstand a person standing directly thereon with shoes on; and
    a power source engaging the UV LED array;
    wherein the LED array is configured to lay beneath the top surface of the transparent protective cover and below a foot receiving portion thereof to irradiate at least a portion of a bottom surface of a shoe positioned on the protective cover with at least some electromagnetic waves with wavelengths between 100 nm and 300 nm.

2. The floor mat of claim 1, wherein the power source is batteries.

3. The floor mat of claim 2, wherein the base is configured to receive the batteries.

4. The floor mat of claim 1, wherein the polyurethane is a cured, two-part polymer.

5. The floor mat of claim 1, wherein polyurethane is an acrylic polyurethane.

6. The floor mat of claim 1, wherein the polyurethane is flexible.

7. The floor mat of claim 1, wherein the protective cover is tacky.

8. The floor mat of claim 1, further including a pressure sensor for activating the UV LED array with the power source, the pressure sensor responsive to a weight on the protective cover.

9. The floor mat of claim 1, wherein the protective cover includes indicia of shoes.

10. The floor mat of claim 1, further comprising a sensor configured to detect the location of a shoe bottom on the protective surface.

11. The floor mar of claim 10, further comprising a controller configured to control the UV LEDs in response to input from the sensor such that the UV LEDs that do not illuminate the shoe bottom are not turned on.

12. The floor mat of claim 1, further comprising a capacitive sensor adapted to sense whether skin is contacting the protective cover.

13. The floor mat of claim 12, further comprising a controller configured to prevent operation of the LED array if skin is contacting the protective cover.

* * * * *